April 11, 1972 M. TANTAU Plant Pat. 3,103
ROSE PLANT
Filed Jan. 22, 1970
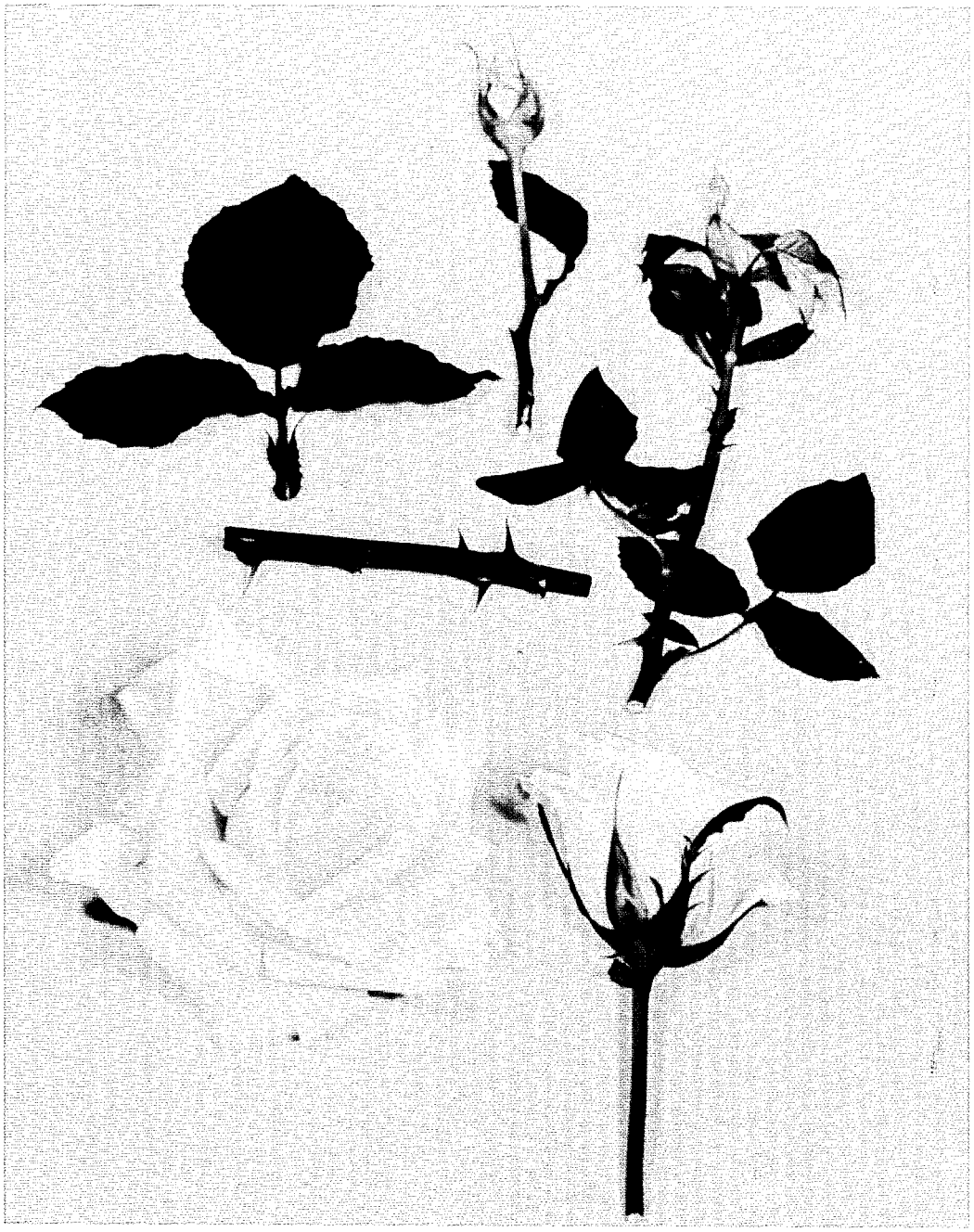
Inventor.
Mathias Tantau
By: Robb & Robb
Attorneys.

United States Patent Office

Plant Pat. 3,103
Patented Apr. 11, 1972

3,103
ROSE PLANT

Mathias Tantau, Uetersen, Germany, assignor to Jackson & Perkins Company, Newport Beach, Calif.

Filed Jan. 22, 1970, Ser. No. 5,164
Claims priority, application Germany, Feb. 18, 1969, 45/69 S
Int. Cl. A01h *5/00*
U.S. Cl. Plt.—24 1 Claim The present invention relates to a new and distinct variety of rose plant of the floribunda class, which was originated by me by crossing the rose variety known in Europe as "Whiskey Mac" (unpatented) with the rose variety known as "Zorina" (U.S. Plant Patent No. 2,321), the former being the seed parent and the latter being the pollen parent.

The primary objective of this breeding was to produce a new and improved rose variety of the floribunda class which has a healthy and vigorous plant habit and which bears attractive yellow flowers in good abundance and suitable for commercial cut flower production when grown under glass. This objective was fully achieved, along with other desirable improvements, as evidenced by the following unique combination of characteristics which are outstanding in the new variety and which distinguish it from its parents, as well as from all other rose varieties of which I am aware:

(1) A bushy, upright, well-branched and compact plant habit;
(2) Strong dark green foliage of medium size and which is slightly reddish green when young;
(3) Intensely bright, light golden yellow flower buds of well pointed form;
(4) Mature, densely filled, fragrant flowers of medium size and abundantly borne in clusters suitable for cut flower production under glass;
(5) A distinctive and attractive deep yellow open flower color which is retained without appreciable fading as the flowers age;
(6) Good resistance to blackspot and powdery mildew; and
(7) Good lasting qualities of the flowers as cut flowers, with a rapid repeating habit of the flowers when grown under glass.

Asexual reproduction of my new rose variety, as performed by me by budding at Uetersen, Germany, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new rose variety, with color terminology in accordance with Hickethier's color standards, except where general color terms of ordinary dictionary significance are obvious:

Parentage: Seedling.
*Seed parent.*—"Whisky Mac."
*Pollen parent.*—"Zorina."

Classification:

*Botanical.*—Rosa hybrid.
*Commercial.*—Floribunda.

Propagation: Holds its distinguishing characteristics through succeeding propagations by budding.

*FLOWER*

(Observations made from specimens grown in greenhouse at Uetersen, Germany.)

Blooming habit: Recurrent.—Continuous.

Bud:

*Size.*—Medium.
*Form.*—Pointed ovoid.
*Color.*—When sepals first divide.—Deep golden yellow, Plate 720.
When half-blown—Inside of petals—Clear yellow, but slightly golden, Plate 710.
Reverse of petals—Light yellow, Plate 610.
*Sepals.*—Normally appendaged; smooth edge. Color—Inside—Apple green, Plate 523, but covered with grayish tomentum. Outside—Dark apple green, Plate 603, with light brown spots at base.
*Receptacle.*—Color—Apple green, Plate 704. Shape—Funnel. Size—Small. Surface—Smooth.
*Peduncle.*—Length—Medium. Surface—Smooth; few very small prickles. Strength—Erect. Color—Medium green. Plate 713.
*Opening.*—Petals curl when folding outwardly.

Bloom:

*Size.*—Medium. Average size when fully expanded—3 inches.
*Borne.*—Several together in pyramidal clusters.
*Stems.*—Medium length; normal strength.
*Form (when first open).*—High-centered. Permanence—Retains its form to the end, but outer petals curl back.
*Petalage.*—Number of petals under normal conditions—From 35 to 38.
*Color.*—Center of flower—Upper surface of petals—Golden yellow, Plate 900. Reverse surface of petals—Yellow, Plate 800. Outer petals—Upper surface—Yellow, Plate 500. Reverse surface—Light Yellow, Plate 400. Base of petals—Small area of Chrome Yellow, Plate 720. General tonality from a distance—Deep yellow. Variegations—Outer petals turn slightly pale yellow.
*Discoloration.*—Very little change to pale yellow through third day.
Petals:
*Texture.*—Thin; leathery.
*Surface.*—Inside—Satiny. Reverse—Satiny.
*Shape.*—Oval.
*Form.*—Tips slightly recurved; moderately quilled.
*Arrangement.*—Imbricated.
*Petaloids in center.*—Few; small.
*Persistence.*—Drop off cleanly.
*Lasting quality.*—On the plant—Long. As cut flower—Very long.
*Fragrance.*—Moderate. Nature.—Fruity.

*Reproductive organs*

Anthers: Medium size; many; arranged regularly around styles. Color—Yellow.
Filaments (threads): Some long, and some medium length. Color—Yellow.
Pollen: Color—Lemon yellow.
Styles: Columnar; bunched; uneven length.
Stigmas: Color—Light yellow.
Ovaries: All enclosed in calyx.
Fruit: Round-headed; seeds protruding.
*Surface.*—Scurfy.
*Color (at maturity).*—Gray.
*Sepals.*—Recurved.

*Plant*

Form: Bush.
Growth: Vigorous.
Habit: Similar to that of "Zorina," but harder wood.
Foliage: Compound of 5 leaflets on normal mid-stem leaves.
*Size.*—Medium.
*Quantity.*—Normal abundance.
*Color.*—New foliage—Light reddish green. Old foliage—Upper side—Dark green, Plate 847. Lower side—Green, Plate 624.
*Leaflets.*—Size—Normal. Shape—Oval pointed. Texture—Upper side—Leathery. Under side—Smooth. Ribs and veins—Ordinary. Edge—Serrated. Serration—Single; sharp. Petiole—Color—Green. Under side—Prickly. Stipules—Medium length; serrated.
*Disease resistance.*—Average resistance to powdery mildew and blackspot, as compared with other varieties grown under the same normal conditions at Uetersen, Germany.
Wood:
*New wood.*—Color—Light green, Plate 903. Bark—Smooth.
*Old wood.*—Color—Green, Plate 625. Bark—Smooth.
Thorns:
*Thorns.*—Quality.—On main stalks from base—Ordinary. On laterals from stalk—Few. Form—Long; straight; narrow base. Color (when young)—Transparent green and red. Position—Irregular.
*Prickles.*—Quantity—Few on main stalks. Color—Brown.
*Short needles.*—Quantity—On main stalks—Few. On laterals—None.

I claim:

1. A new and distinct variety of rose plant of the fluoribunda class, substantially as herein shown and described, characterized particularly as to novelty by the unique combination of a bushy, upright, well-branched and compact plant habit, strong dark green foliage of medium size and which is slightly reddish green when young, intensely bright, light golden yellow flower buds of well pointed form, mature, densely filled, fragrant flowers of medium size and abundantly borne in clusters suitable for cut flower production under glass, a distinctive and attractive deep yellow open flower color which is retained without appreciable fading as the flower age, good resistance to blackspot and powdery mildew, and good lasting qualities of the flowers as cut flowers, with a rapid repeating habit of the flowers when grown under glass.

No references cited.

ROBERT E. BAGWILL, Primary Examiner